(12) United States Patent
Siminou

(10) Patent No.: US 6,637,881 B1
(45) Date of Patent: Oct. 28, 2003

(54) EYECUP SHIELD WITH FINGER PORTS

(75) Inventor: Kamran Siminou, Newport Beach, CA (US)

(73) Assignee: Neuroptics, Inc., Irvine, CA (US)

( * ) Notice: Subject to any disclaimer, the term of this patent is extended or adjusted under 35 U.S.C. 154(b) by 0 days.

(21) Appl. No.: 10/079,771

(22) Filed: Feb. 19, 2002

Related U.S. Application Data

(63) Continuation of application No. 10/037,617, filed on Jan. 2, 2002.

(51) Int. Cl.⁷ ................................................. A61B 3/00
(52) U.S. Cl. ..................................................... 351/200
(58) Field of Search ................................ 351/200, 219, 351/205, 246, 247; 359/601; 600/489; 294/1.2

(56) References Cited

U.S. PATENT DOCUMENTS

| | | | | |
|---|---|---|---|---|
| 3,903,871 A | * | 9/1975 | Chisum et al. | 600/489 |
| 5,408,359 A | * | 4/1995 | Ferrett et al. | 359/601 |
| 5,649,727 A | * | 7/1997 | St. Louis | 294/1.2 |

* cited by examiner

Primary Examiner—George Manuel
(74) Attorney, Agent, or Firm—Stephanie L. Seidman; Mikael Havluciyan; Heller Ehrman White & McAuliffe, LLP

(57) ABSTRACT

An eyecup shield for use during ocular examinations. The eyecup shield is formed from a cylindrical member having a proximal end with an opening, a distal end with an opening, and a wall. The wall is substantially rigid and has one or more access ports which are sized to receive a finger.

41 Claims, 5 Drawing Sheets

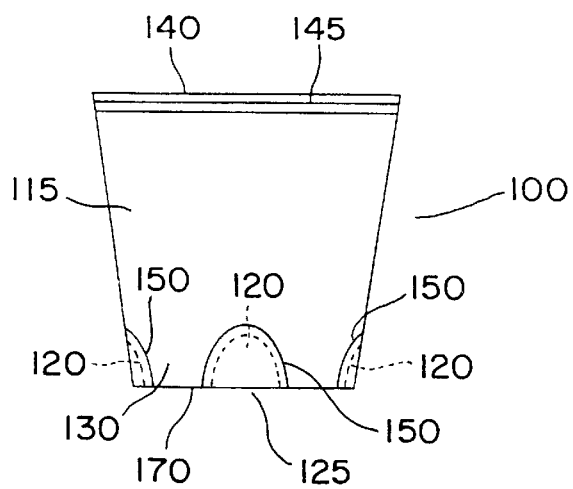
FIG. 8
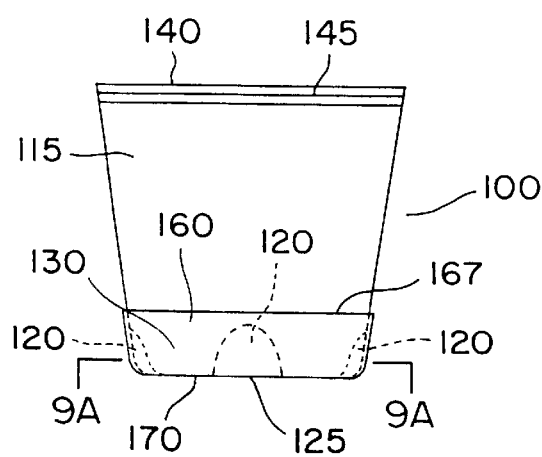 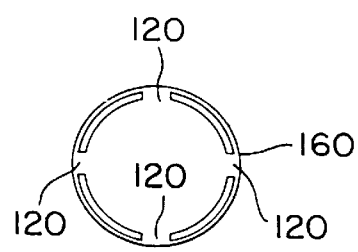
FIG. 9　　FIG. 9A

EYECUP SHIELD WITH FINGER PORTS

BACKGROUND OF THE INVENTION

This is a continuation of U.S. application Ser. No. 10/037,617, filed Jan. 2, 2002, which is incorporated herein by reference.

FIELD OF THE INVENTION

The present invention generally relates to eyecup shields used to shield an eye or eyes from ambient light during ocular examinations. More particularly, the present invention relates to eyecup shields with finger ports to allow manipulation of the eye during examination. Furthermore, the present invention relates to eyecup shields with finger ports and disposable opaque covers.

BACKGROUND OF THE INVENTION

Pupillary response must be measured as part of the neurological evaluation of patients or subjects during testing or examination. Adverse conditions including direct light may diminish the ability of optometrists, ophthalmologists, nurses, critical care doctors, emergency doctors, neurosurgeons, other caregivers, or examiners to take reliable measurements and to acquire accurate response data. Changing light conditions have the potential to bias results thus masking important findings or indicating false positives. The incorporation of a shield or eyecup can prevent some of the negative effects of the adverse conditions. However, in unresponsive or non-cooperative patients, the need exists to hold the eyelid open making the use of eyecups impractical or impossible. And even in responsive patients, the caregiver may need to manipulate the eye during the exam, and this again makes the use of eyecups impractical or impossible.

Known eyecups restrict access to the eye because they surround the eye. Therefore, eyecups can only be used on conscious and responsive patients, and when the need to manipulate or prop the eyes open with a medical device or fingers arises, the eyecup must be removed. Current eyecups are therefore inappropriate for data acquisition when used on patients whose eyes must be manipulated by the caregiver during the examination. Therefore, a need exists for eyecup shields that enable physicians and other caregivers to physically manipulate the eye while shielding it from ambient light.

SUMMARY OF THE INVENTION

In one particularly innovative aspect, the invention comprises an eyecup shield with access ports that allow for the eyelid of a patient to be manually manipulated or opened during the acquisition of pupillary response data. The device is structured so that the eye being measured is shielded from ambient light, while permitting finger access or medical device access to the eyelid.

The eyecup shield comprises a barrel that can be substantially cylindrical or frustoconical, having one end adapted for coupling to a pupilometer or other ocular examination equipment, while the other end can be adapted for placement around a patient's or subject's eye. The barrel has a lumen and an outer wall. The wall of the barrel can be substantially rigid and can be made of an opaque material or any material that is substantially impervious to light. The eyecup shield can have one, two, three, four, five, or more access ports disposed around its distal end, enabling a physician, caregiver, or examiner access to a patient's or subject's eye while using the eyecup shield.

In one embodiment, the eyecup shield has two access ports that are diametrically opposed. In another embodiment, the eyecup shield has four access ports that are spaced at equal intervals. The access ports can be disposed such that the center or axis of each access port lies on one plane in the distal region of the eyecup shield. Alternatively, the access ports can be staggered so that their centers are not all on the same plane. A flexible ring can be coupled to the distal end of the eyecup shield for added comfort to the patient and for adaptability of the eyecup shield to the contours of any patient's or subject's face. The flexible ring can be made of foam or any other soft and malleable material and can be sterile and disposable for added safety.

In accordance with another embodiment, the eyecup shield can include opaque patches covering the access ports further limiting the entry of light into the field of view of the eye during use. The patches can be made of a material that is flexible and substantially impervious to light. For example, they can be latex and tinted a color, such as black, that limits the influx of light. The patches can be coupled to the eyecup shield using an adhesive to secure them either to the outer wall of the eyecup shield or to the inner wall or both. Alternatively, they can be stitched, stapled, or coupled in any manner known to those skilled in the art. The patches can be disposable and sterile allowing for a sanitary approach to open or manipulate an eye. The patches can be flat, or they can be shaped to form a lumen. In either case, they can be flexible, thus allowing for the insertion of fingers or medical devices into the lumen of the barrel without penetrating the patches. A doctor, caregiver or examiner is therefore able to manipulate a patient's or subject's eye in a sterile environment.

In accordance with yet another embodiment, the eyecup shield can be used in combination with a disposable jacket or cover rather than patches. The disposable jacket can be made of a material that is flexible and substantially impervious to light. For example, it can be latex and tinted a color, such as black, that limits the influx of light. The disposable jacket is slipped over the distal end of the eyecup shield and over the one or more access ports. The disposable jacket can be frictionally engaged with the outer wall of the eyecup shield or it can be glued, stitched, stapled or coupled in any other manner known to those skilled in the art. The proximal and distal ends of the jacket can have collars that secure the jacket to the outer wall of the eyecup shield.

The jacket can be formed from a flat latex sheet that is joined at its ends to form a latex cylinder or frustocone depending on the shape of the eyecup. The sheet should be wide enough to cover the access ports and long enough so that the cylinder or frustocone formed by joining the ends of the sheet has a diameter that is the same or slightly smaller than the diameter of the distal end of the eyecup. Alternatively, the latex sheet can have preformed protuberances that extend slightly through the access ports of the eyecup when the sheet is formed into a cylinder or frustocone.

In another embodiment, the invention is directed to an eyecup shield that can be placed over a caregiver's fingers while the caregiver or examiner is propping open or manipulating a patient's or subject's eye. The eyecup shield can be cylindrical or frustoconical, with a proximal end that is adapted for attachment to an ocular examination device such as a pupilometer or ophthalmoscope, while the distal end is adapted for engagement with a patient's or subject's face. The distal end includes a distal rim forming one or more arches for finger or medical device access. The distal rim can have one, two, three, four, five or more arches along its perimeter. In case of two or more arches, they can be spaced in any manner. In one embodiment, the eyecup shield has two arches that are diametrically opposed. In another embodiment, the eyecup shield has four arches spaced along the distal rim in equal intervals.

In another embodiment, the arches can be covered with patches, similar to those described above and coupled to the eyecup shield in the same manner as described above. In an alternative embodiment, the arches can be covered with a disposable jacket similar to the one described above and coupled to the eyecup shield in the same manner as described above.

In another embodiment, the invention is directed to an eyecup shield comprising a substantially rigid cylinder or frustocone with a substantially flexible skirt coupled concentrically around its distal end. The flexible skirt can be frictionally engaged with the distal end of the eyecup shield or it can include a collar that holds the skirt to the distal end of the eyecup shield.

The cylinder can be made of an opaque material or any material that is colored or adapted to be substantially impervious to light. Likewise the flexible skirt can also be made of an opaque material or any material that is colored or adapted to be substantially impervious to light. The flexible skirt can be disposable. The skirt is flexible and gives way to pressure without rupturing, such as lateral pressure exerted by the insertion of one or more fingers. Thus, a caregiver or examiner can prop open or manipulate a patient's or subject's eye through the skirt while the eyecup shield is maintained in position to block out ambient light. This enables a caregiver or examiner to manipulate a patient's or subject's eye in a sterile environment that is also substantially free of ambient light.

Other objects and features of the present invention will become apparent from consideration of the following description taken in conjunction with the accompanying drawings.

BRIEF DESCRIPTION OF THE DRAWINGS

Reference is next made to a brief description of the drawings, which illustrate embodiments of eyecup shields. The drawings and detailed description which follow are intended to be merely illustrative and are not intended to limit the scope of the invention as set forth in the appended claims.

FIG. 8 is a side elevation view of the eyecup shield of FIG. 7 with associated patches.

FIG. 9 is a side elevation view of the eyecup shield of FIG. 7 with associated jacket.

FIG. 9A is a cross-sectional view taken through section line 9A—9A of the eyecup shield depicted in FIG. 9.

DETAILED DESCRIPTION OF PREFERRED EMBODIMENTS

Figure 1:
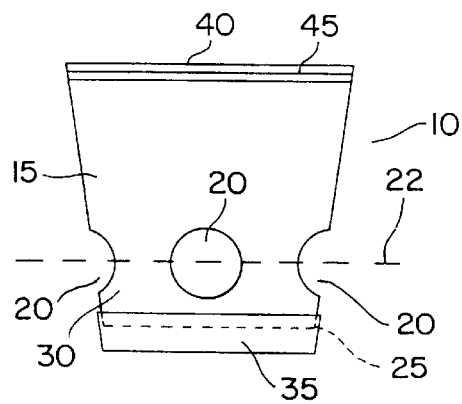
FIG. 1 is a side elevation view of an eyecup shield according to one embodiment.
Figure 2:
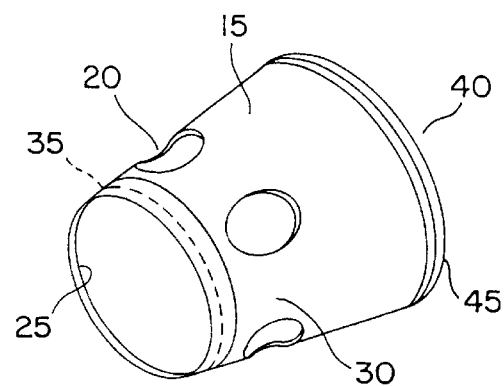
FIG. 2 is a perspective view of the eyecup shield depicted in FIG. 1.

Turning now to the drawings, FIG. 1 provides a side elevational view of an eyecup shield 10 in accordance with the present invention. And FIG. 2 provides a perspective view of the same eyecup shield 10. The main component of the eye cup shield 10 is an unibody barrel 15, which can be made of any molded material, such as plastic, urethane, rubber, or any other material that can be formed into a substantially rigid barrel. The barrel 15 may be formed by a compression molding process, a transfer molding process, a casting process, an injection molding process, or similar process. The material of the barrel 15 is opaque and substantially impervious to light. For example, it can be coated with a color that prevents the influx of light, or it can preferably be black. The barrel 15 can be frustoconical, as shown in the figures, or it can be cylindrical.

Figure 11:
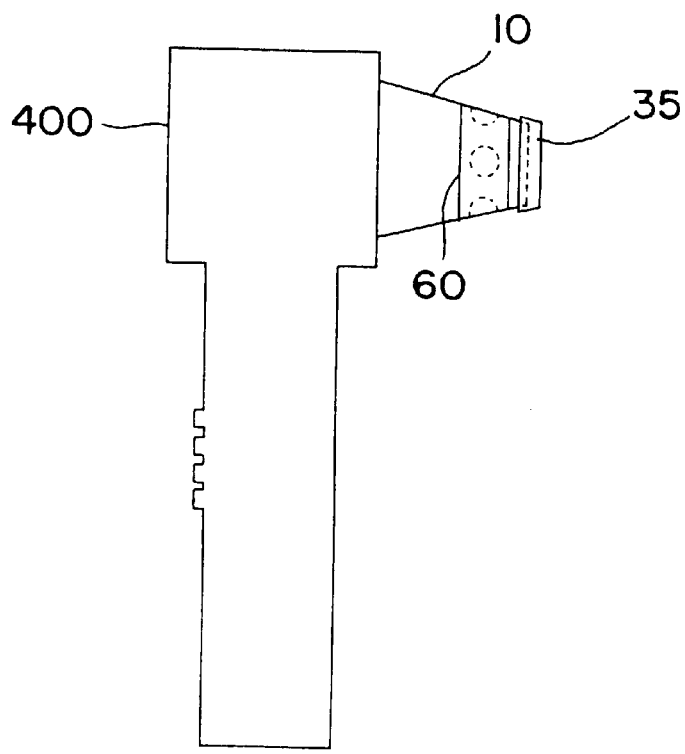
FIG. 11 is a side elevation view of a pupilometer with associated eyecup shield.

The proximal end of the barrel 40 is open and is adapted for attachment to an ocular examination device, such as a pupilometer, ophthalmoscope, glaucometer or any other ocular examination device. The proximal end of the barrel can include threads 45 for attachment to an ocular examination device. In the Figures, the threads 45 are depicted as being on the outer wall of the barrel 15, but they can instead be on the inner wall of the barrel 15. In either case, the threads 45 can be mated to threads on an ocular examination device. FIG. 11, for example, shows the eyecup shield 10 secured to a pupilometer 400.

The eyecup shield 10 includes access ports 20, which are sized to receive a person's fingers in particular, but also certain medical devices. The access ports 20 can be positioned around the eyecup shield 10 in distal region 30 of the eyecup shield. As shown in FIG. 1, the access ports 20 can be level with one another, i.e., positioned along the same horizontal plane 22. Alternatively, the access ports 20 can be staggered (not shown). The eyecup shield 10 shown in FIGS. 1 and 2 has four diametrically opposed access ports 20, but it can have one, two, three, five or more access ports 20. Furthermore, the access ports need not be diametrically opposed.

Fitted over the distal end 25 of the eyecup shield 10 is a flexible ring 35. The flexible ring 35 can be made of a biocompatible foam, rubber, plastic, urethane, or any material that can be formed into a compliant and flexible ring. The flexible ring 35 can be disposable and secured to the distal end 25 of the eyecup shield 10 by frictional engagement.

Alternatively, it can be glued or secured in any other way known to those skilled in the art. The material of the flexible ring 35 is opaque and substantially impervious to light. For example, it can be coated with a color that prevents the influx of light, or it can preferably be black.

Figure 3:
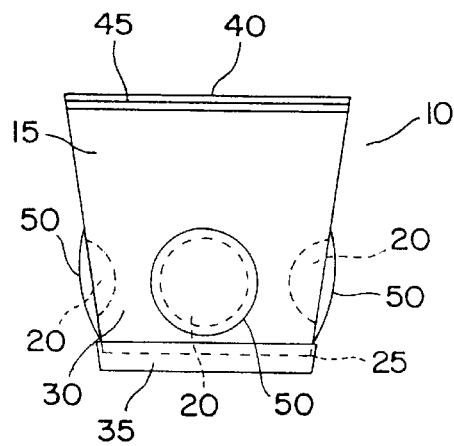
FIG. 3 is a side elevation view of the eyecup shield of FIGS. 1 and 2 with associated patches.
Figure 3A:
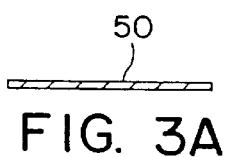
FIG. 3A is a side cross-sectional view of the patch depicted in FIG. 3.

Turning now to FIG. 3, the access ports 20 of eyecup shield 10 are covered by patches 50, which further limit the entry of light into the field of view of the eye during use of the eyecup shield 10. The patches 50 can be made of a material that is flexible and substantially impervious to light. For example, they can be latex and tinted a color, such as black, that limits the influx of light. The patches 50 can be coupled to the eyecup shield 10 by using an adhesive to secure them either to the outer wall of the barrel 15 (as shown) or to the inner wall of the barrel (not shown) or to both the inner and outer walls of the barrel (not shown). Alternatively, the patches 50 can be stitched, stapled, or coupled in any manner known to those skilled in the art. The patches 50 can be disposable and sterile allowing for a sanitary approach to open or manipulate an eye. The patches 50 can be substantially flat as shown in FIGS. 3 and 3A. Patches 50 are flexible and have great tensile strength, allowing a caregiver or examiner to manipulate the eye or open a patient's or subject's eyelids without rupturing a patch 50.

Figure 3B:
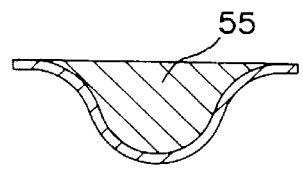
FIG. 3B is a side cross sectional view of a patch according to another embodiment.

Alternatively, as shown in FIG. 3B, patches 55 can be used instead of patches 50. Patches 55 are shaped to form a lumen allowing for the insertion of a person's fingers or medical devices. The luminal patches 55 can protrude slightly into the lumen of the barrel 15, thus enabling a caregiver or examiner to insert his finger or fingers into the lumen of the patch 55 and manipulate a patient's or subject's eye in a sterile environment.

Figure 4:
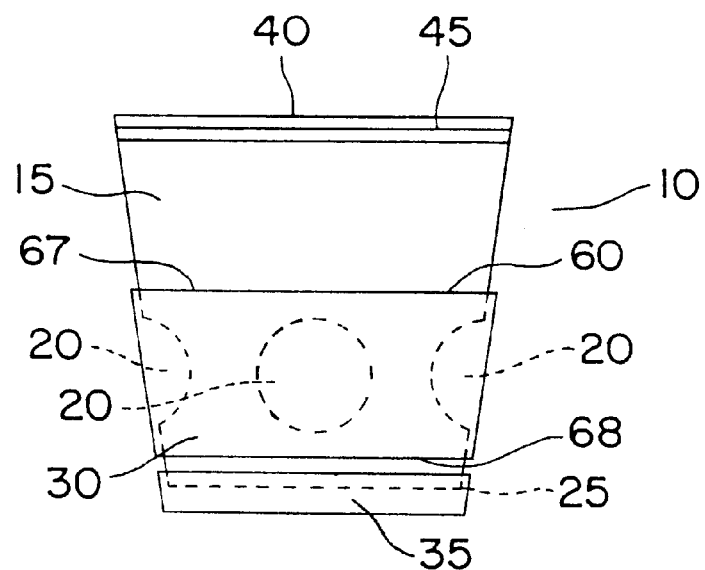
FIG. 4 is a side elevation view of the eyecup shield of FIGS. 1 and 2 with associated jacket.

FIG. 4 shows the eyecup shield 10 used in combination with a disposable jacket 60 instead of patches 50. The disposable jacket is slipped over the distal region 30 of the barrel 15, thus covering the access ports 20. The disposable jacket 60 can be formed from a flat material, such as latex, which is sealed at its ends, thus forming a cylindrical or frustoconical shape. The disposable jacket 60 also has great tensile strength able to bear substantial longitudinal forces caused by the pressure exerted by a doctor's or caregiver's fingers without rupturing.

Figure 5:
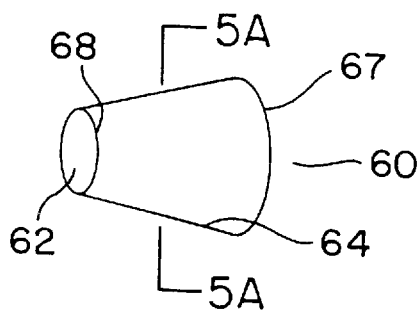
FIG. 5 is a perspective view of the jacket depicted in FIG. 4.
Figure 5A:
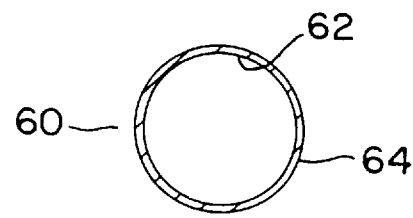
FIG. 5A is a cross-sectional view taken through section line 5A—5A of the jacket depicted in FIG. 5.

As shown in FIGS. 5 and 5A, the jacket 60 includes a lumen 62 and an outer wall 64. The lumen 62 can be coated with an adhesive except in the areas that cover the access ports 20. Alternatively, the proximal and distal edges of the jacket 60 can include collars 67 and 68 respectively, to secure the jacket 60 to the distal region 30. The collars 67 and 68 can be less flexible than the main body of the jacket 60 and can be sized for a tight fit around the barrel 15. Alternatively, the jacket 60 can be secured to the distal region 30 merely through frictional engagement.

In still another embodiment, the jacket 60 can be secured to the lumen of the barrel 15 rather than being slipped over the outer wall of the barrel 15. The jacket 60 can be secured to the lumen of the barrel 15 by applying an adhesive to the outer wall of the jacket 60 and securing the outer wall of the jacket to the lumen of the barrel. Alternatively, the jacket 60 can be stitching, stapled or secured to the lumen of the barrel 15 in any manner known to those skilled in the art.

Figure 6:
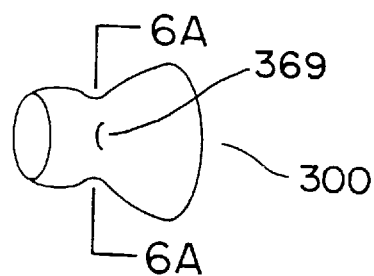
FIG. 6 is a perspective view of an eyecup shield jacket according to another embodiment.
Figure 6A:
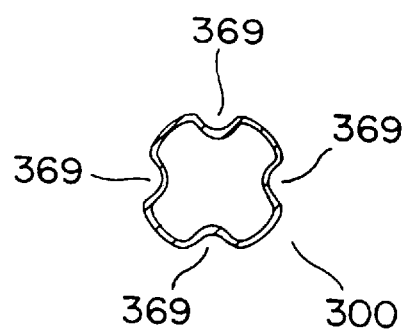
FIG. 6A is a cross-sectional view taken through section 6A—6A of the jacket depicted in FIG. 6.

In an alternative embodiment of the jacket 300 as shown in FIG. 6, the jacket 300, includes inwardly biased protuberances 369 that can be positioned over the access ports 20. The protuberances 369, like patches 55, can protrude slightly into the lumen of the barrel 15 of the eyecup shield 10, thus enabling a caregiver or examiner to insert his finger or fingers into the lumen of the protuberances 469 and manipulate a patient's or subject's eye in a sterile environment. FIG. 6A shows a cross-section of the jacket 300 showing the protuberances 369 projecting inwardly.

Figure 7:
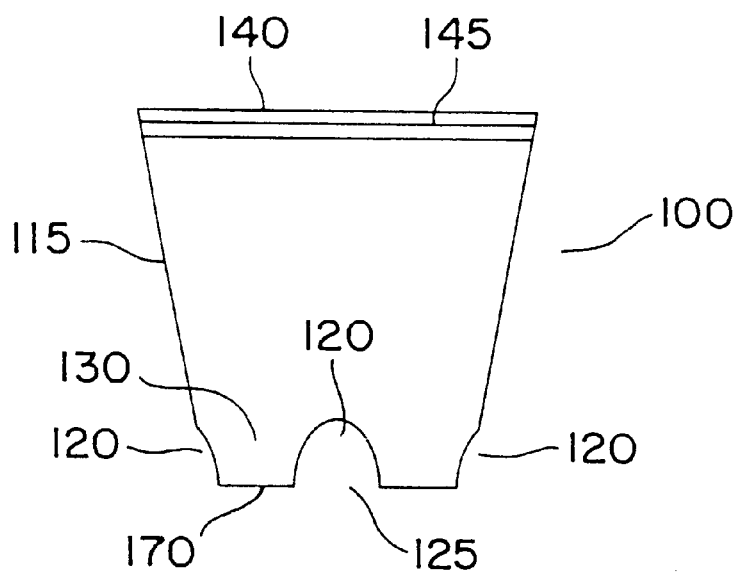
FIG. 7 is a side elevation view of an eyecup shield according to another embodiment.

FIG. 7 shows another embodiment of an eyecup shield 100. The eyecup shield 100 includes a barrel 115 formed from a substantially rigid material as the eyecup shield 10 of FIGS. 1–4. The eyecup shield 100 is shown as being frustoconical in FIG. 7, but as before, it can be cylindrical as well. The material of the barrel 115 is again opaque and substantially impervious to light. The eyecup shield 100 is open at both its distal 125 and proximal 140 ends. The proximal end 140 can include threads 145 for securing the eyecup shield 100 to an ocular examination device, such as a pupilometer, glaucometer, or ophthalmoscope.

The main difference between eyecup shield 100 and eyecup shield 10, is that eyecup shield 100 includes one or more arches 120 cut into the rim 170 of the eyecup shield 100. The arches 120 are sized to allow for placement of the arches 120 over a doctor's or caregiver's fingers. The eyecup shield 100 can have one, two, three, four, five, or more arches 120 cut into its rim 170. In case of an even number of arches 120, the arches 120 can be diametrically opposed. Alternatively, they can be spaced in any manner, such as being spaced at equal intervals.

As shown in FIG. 8, the arches 120, can be covered with patches 150, which are the same or similar in material to patches 50. The patches 150 form a flexible and compliant wall over arches 120, further limiting the entry of light into the field of view of the eye during use of the eyecup shield 100. Patches 150 are flexible enough to conform to the contours of a finger when the eyecup shield 100 is placed over a doctor's or caregiver's finger(s). Like patches 50, The patches 150 can be coupled to the eyecup shield 100 using an adhesive to secure them either to the outer wall of the barrel 115 (as shown) or to the inner wall of the barrel 115 (not shown) or to both the inner and outer walls of the barrel 115 (not shown). Alternatively, the patches 150 can be stitched, stapled, or coupled in any manner known to those skilled in the art. The patches 150 can be disposable and sterile allowing for a sanitary approach to open or manipulate an eye. The patches 150 can be substantially flat. Alternatively, they can be shaped to form a lumen allowing for the insertion of fingers or medical devices, similar to the patches 55 shown in FIG. 3B, in which case, they can protrude slightly into the lumen of the barrel.

FIG. 9 shows the eyecup shield 100 used in combination with a disposable jacket 160 instead of patches 150. The disposable jacket is slipped over the distal end 125 of the barrel 115, thus covering the arches 120. Like disposable jacket 60, disposable jacket 160 can be formed from a flat material, such as latex, which is sealed at its ends, thus forming a cylindrical or frustoconical shape. The lumen of jacket 160 (not shown) can be coated with an adhesive except in the areas that cover the arches 120. Alternatively, the proximal edge of the jacket 160 can include a collar 167 to secure the jacket 160 to the distal region 130 of the barrel 115. The collar 167 can be less flexible than the main body of the jacket 160 and can be sized to fit tightly over the barrel 115. Alternatively, the jacket 160 can be secured to the distal region 130 of the barrel 115 merely through frictional engagement. FIG. 9A shows how the jacket 160 covers the distal region 130 of the barrel 115 and the arches 120.

Figure 10:
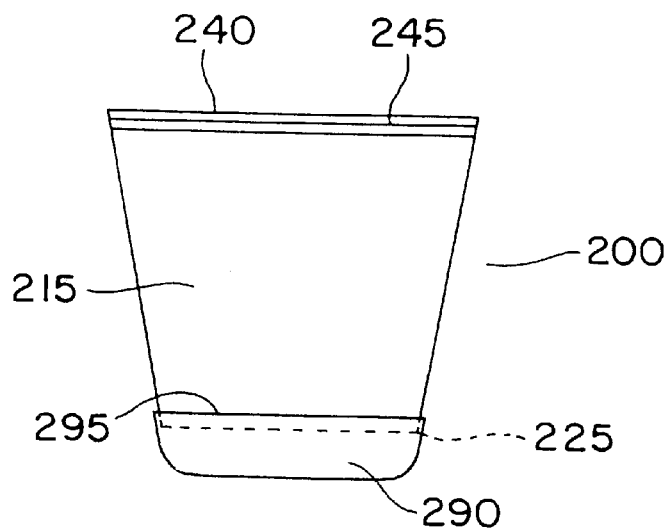
FIG. 10 is a side elevation view of an eyecup shield according to another embodiment.

FIG. 10 shows another embodiment of an eyecup shield 200. The eyecup shield 200 again includes a barrel 215 as its main component. The barrel 215 can be shaped as a frustocone (as shown) or as a cylinder (not shown). The proximal end 240 and the distal end 225 of the barrel 215 are open. The proximal end 240 is adapted for attachment to an ocular examination device, such as a pupilometer, glaucometer, or ophthalmoscope. Threads 245 can be either on the outer wall of the barrel 200 (as shown) or on the lumen of the barrel 200.

Used in combination with the eyecup shield 200 is flexible skirt 290, which is coupled concentrically around the distal end 225 of the barrel 215. The flexible skirt 290 can be disposable and can be made of an opaque material or any material that is colored or adapted to be substantially impervious to light. The skirt 290 is flexible and gives way to pressure, such as lateral pressure exerted by the insertion of one or more fingers. Thus, a caregiver or examiner can insert fingers past the skirt 290 and prop open or manipulate a patient's or subject's eye while the eyecup shield 200 is maintained in position to block out ambient light. The skirt 290 can be frictionally secured to the distal end 225 of the barrel 215. Alternatively, the proximal end of the skirt 290 can have a collar 295 which is adapted to fit tightly around the distal end 225 of the barrel 215.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

I claim:

1. An eyecup shield, the eyecup shield comprising a barrel having a proximal end with an opening, a distal end with an opening, and a wall, wherein the wall is substantially rigid and comprises a first access port sized to receive a finger and a second access port sized to receive a finger.

2. The eyecup shield of claim 1, wherein the first and second access ports are diametrically opposed.

3. The eyecup shield of claim 2, wherein the wall further comprises a third access port, said third access port sized to receive a finger, wherein said third access port is positioned along the same plane as the first and second access ports.

4. The eyecup shield of claim 3, wherein the wall further comprises a fourth access port, said fourth access port sized to receive a finger, wherein the third and fourth access ports are diametrically opposed.

5. The eyecup shield of claim 1, wherein the barrel comprises a proximal region and a distal region, and the first and second access ports are in the distal region.

6. The eyecup shield of claim 5, further comprising a jacket disposed circumferentially around the distal region of the barrel, the jacket forming a cover around the distal region and the access ports, wherein the jacket comprises a flexible material.

7. The eyecup shield of claim 6, wherein the jacket comprises a material that is substantially impervious to light, said jacket being sterile and disposable.

8. The eyecup shield of claim 1, wherein the proximal end of the barrel is adapted for attachment to an ocular examination device.

9. The eyecup shield of claim 8, wherein the ocular examination device comprises a pupilometer examination device comprises an ophthalmoscope.

10. The eyecup shield of claim 8, wherein the ocular.

11. The eyecup shield of claim 8, wherein the ocular examination examination device comprises an ophthalmoscope.

12. The eyecup shield of claim 1, wherein the barrel is frustoconical.

13. The eyecup shield of claim 1, further comprising one or more patches covering the first and second access ports, said one or more patches comprising a flexible material.

14. The eyecup shield of claim 13, wherein the one or more patches are opaque.

15. The eyecup shield of claim 13, further comprising means for detachably coupling the one or more patches to the eyecup shield, and wherein the one or more patches are disposable.

16. The eyecup shield of claim 1, further comprising a ring detachably coupled to the distal end of the barrel, said ring extending distal to the distal end of the barrel.

17. The eyecup shield of claim 1, wherein the barrel comprises a material that is substantially impervious to light.

18. An eyecup shield for use during ocular examinations, said eyecup shield comprising:

a barrel having a proximal region with a proximal end having an opening, a distal region with a distal end having an opening, and a wall comprising a substantially rigid material that is substantially impervious to light, wherein the wall comprises at least one access port at the distal region, said access port sized to receive a finger, and wherein the proximal end is adapted for attachment to an ocular examination device;

at least one patch covering said at least one access port, said patch detachably coupled to the barrel; and a flexible ring, said flexible ring detachably coupled to the distal end of the barrel.

19. The eyecup shield of claim 18, wherein the patch is opaque.

20. The eyecup shield of claim 18, wherein the flexible ring is opaque.

21. The eyecup shield of claim 20, wherein the flexible ring is sterile and disposable.

22. The eyecup shield of claim 18, wherein the wall of the barrel comprises at least two access ports.

23. The eyecup shield of claim 18, wherein the wall of the barrel comprises at least four access ports.

24. The eyecup shield of claim 18, wherein the patch is sterile and disposable.

25. The eyecup shield of claim 18, wherein the barrel is frustoconical.

26. An eyecup shield for use during ocular examination, said eyecup shield comprising:

a barrel having a proximal end with an opening, a distal end with an opening, and a wall, wherein the wall is substantially rigid and wherein the proximal end is adapted for attachment to an ocular examination device; and a flexible skirt having a proximal end and a distal end, the proximal end coupled concentrically around the distal end of the barrel, said skirt comprising a material that is substantially impervious to light.

27. The eyecup shield of claim 26, wherein the barrel is frustoconical.

28. The eyecup shield of claim 26, wherein the barrel comprises a material that is substantially impervious to light.

29. An eyecup shield, the eyecup shield comprising a barrel having a proximal end with an opening, a distal end with an opening, and a wall, wherein the wall is substantially rigid and comprises an access port sized to receive a finger, and wherein the proximal end of the barrel is adapted for attachment to an ocular examination device.

30. The eyecup shield of claim 29, wherein the barrel comprises a proximal region and a distal region, and the access port is in the distal region.

31. The eyecup shield of claim 30, further comprising a jacket disposed circumferentially around the distal region of the barrel, the jacket forming a cover around the distal region and the access port, wherein the jacket comprises a flexible material.

32. The eyecup shield of claim 31, wherein the jacket comprises a material that is substantially impervious to light, said jacket being sterile and disposable.

33. The eyecup shield of claim 29, wherein the ocular examination device comprises a pupilometer.

34. The eyecup shield of claim 29, wherein the ocular examination devices comprises an ophthalmoscope.

35. The eyecup shield of claim 29, wherein the ocular examination devices comprises a glaucometer.

36. The eyecup shield of claim 29, wherein the barrel is frustoconical.

37. The eyecup shield of claim 29, further comprising a patch covering the access port, said patch comprising a flexible material.

38. The eyecup shield of claim 37, wherein the patch is opaque.

39. The eyecup shield of claim 37, further comprising means for detachably coupling the patch to the eyecup shield, and wherein the patch is disposable.

40. The eyecup shield of claim 29, further comprising a ring detachably coupled to the distal end of the barrel, said ring extending distal to the distal end of the barrel.

41. The eyecup shield of claim 29, wherein the barrel comprises a material that is substantially impervious to light.

* * * * *

UNITED STATES PATENT AND TRADEMARK OFFICE
CERTIFICATE OF CORRECTION

PATENT NO. : 6,637,881 B1
DATED : October 28, 2003
INVENTOR(S) : K. Siminou

It is certified that error appears in the above-identified patent and that said Letters Patent is hereby corrected as shown below:

<u>Columns 7-10,</u>
Claims 9, 10, 11, 16, 34, 35 and 40 should read as follows:

9. The eyecup shield of claim 8, wherein the ocular examination device comprises a pupilometer.

10. The eyecup shield of claim 8, wherein the ocular examination device comprises an ophthalmoscope.

11. The eyecup shield of claim 8, wherein the ocular examination device comprises a glaucometer.

16. The eyecup shield of claim 1, further comprising a ring detachably coupled to the distal end of the barrel, said ring extending distally to the end of the barrel.

34. The eyecup shield of claim 29, wherein the ocular examination device comprises an ophthalmoscope.

35. The eyecup shield of claim 29, wherein the ocular examination device comprises a glaucometer.

40. The eyecup shield of claim 29, further comprising a ring detachably coupled to the distal end of the barrel, said ring extending distally to the distal end of the barrel.

Signed and Sealed this

Twenty-seventh Day of January, 2004

JON W. DUDAS
*Acting Director of the United States Patent and Trademark Office*